US00RE44917E

(19) United States
(12) Reissued Patent
Tuttle et al.

(10) Patent Number: US RE44,917 E
(45) Date of Reissued Patent: May 27, 2014

(54) COMPOSITIONS, KITS AND METHODS FOR INITIATING OR ACCELERATING CURING OF ENDODONTIC FILLER OR SEALER COMPOSITIONS PLACED ON A ROOT CANAL

(71) Applicant: Ultradent Products, Inc., South Jordan, UT (US)

(72) Inventors: Richard D. Tuttle, Layton, UT (US); Jeff A. Wagner, Salt Lake City, UT (US); Neil T. Jessop, Sandy, UT (US); Jaleena Fischer-Jessop, Sandy, UT (US)

(73) Assignee: Ultradent Products, Inc., South Jordan, UT (US)

(21) Appl. No.: 13/722,653

(22) Filed: Dec. 20, 2012

Related U.S. Patent Documents

Reissue of:
(64) Patent No.: 7,863,349
Issued: Jan. 4, 2011
Appl. No.: 11/530,787
Filed: Sep. 11, 2006

(51) Int. Cl.
*A61K 6/08* (2006.01)

(52) U.S. Cl.
USPC ..... 523/116; 433/224

(58) Field of Classification Search
USPC ..... 433/224, 102, 81; 523/116
See application file for complete search history.

(56) References Cited

U.S. PATENT DOCUMENTS 3,082,526 A 3/1963 Nitzche et al.
3,328,880 A 7/1967 Schlesinger
3,715,331 A 2/1973 Molnar
3,882,600 A 5/1975 Plymale
3,925,895 A 12/1975 Kliment et al.

(Continued)

FOREIGN PATENT DOCUMENTS

EP 0821931 2/1998
EP 1375619 1/2004

(Continued)

OTHER PUBLICATIONS

Ventura, G., et al., Morphological changes on gold-coated brass endodontic pins; Instituto di Clinica Odontoiatrica, Universitita degli Studi, Genova; Minerva Stomatol, vol. 44(6), pp. 273-283 (1995).

(Continued)

*Primary Examiner* — Sunil K Singh
(74) *Attorney, Agent, or Firm* — Workman Nydegger

(57) ABSTRACT

Activating endodontic points and dental tools are sized and configured to be placed in the root canal of a tooth. The activating endodontic points or dental tools are coated or impregnated with a curing agent that initiates or accelerates polymerization of a sealer or filler composition when placed in contact with the sealer or filler material. Curing agents can include amines that can destabilize a peroxide in the sealer or filler material to initiate or accelerate polymerization, or they may comprise the peroxide. An implement can be dipped in a concentrated curing composition just prior to inserting the implement into a root canal to contact the filler or sealer composition. Kits may include a plurality of curing agent compositions having different concentrations and/or amounts of curing agent. Kits may also include a curable resin material that includes a first part of a multi-part curing system and a curing composition that includes, as curing agent a complementary part of the curing system.

64 Claims, 6 Drawing Sheets

(56) References Cited

U.S. PATENT DOCUMENTS

| | | | | |
|---|---|---|---|---|
| 3,926,906 | A | 12/1975 | Lee, II et al. | |
| 3,959,212 | A | 5/1976 | Rockett et al. | |
| 3,997,504 | A | 12/1976 | Plymale | |
| 4,182,035 | A | 1/1980 | Yamauchi et al. | |
| 4,240,832 | A | 12/1980 | Jandourek | |
| 4,259,117 | A | 3/1981 | Yamauchi et al. | |
| 4,302,381 | A | 11/1981 | Omura et al. | |
| 4,425,094 | A | 1/1984 | Tateosian et al. | 433/228.1 |
| 4,449,938 | A | 5/1984 | Pollak | |
| 4,499,251 | A | 2/1985 | Omura et al. | |
| 4,515,930 | A | 5/1985 | Omura et al. | |
| 4,525,493 | A | 6/1985 | Omura et al. | |
| 4,539,382 | A | 9/1985 | Omura et al. | |
| 4,612,384 | A | 9/1986 | Omura et al. | |
| 4,657,592 | A | 4/1987 | Takubo | |
| 4,657,941 | A | 4/1987 | Blackwell et al. | |
| 4,657,959 | A | 4/1987 | Bryan et al. | |
| 4,669,983 | A | 6/1987 | Bunker | |
| 4,670,576 | A | 6/1987 | Bunker | |
| 4,732,943 | A | 3/1988 | Beech et al. | |
| 4,806,381 | A | 2/1989 | Engelbrecht et al. | |
| 4,813,876 | A | 3/1989 | Wang | |
| 4,816,495 | A | 3/1989 | Blackwell et al. | |
| 4,872,936 | A | 10/1989 | Engelbrecht | |
| 4,886,843 | A | 12/1989 | Walton | |
| 4,966,934 | A | 10/1990 | Huang et al. | |
| 4,986,754 | A | 1/1991 | Chang et al. | |
| 5,055,497 | A | 10/1991 | Okada et al. | |
| 5,088,497 | A | 2/1992 | Ikeda | |
| 5,089,051 | A | 2/1992 | Eppinger et al. | |
| 5,095,045 | A | 3/1992 | Winkel et al. | |
| 5,108,506 | A | 4/1992 | Yuhda et al. | |
| 5,112,884 | A | 5/1992 | Hanke | |
| 5,132,458 | A | 7/1992 | Honel et al. | 564/367 |
| 5,177,121 | A | 1/1993 | Bunker | |
| 5,192,815 | A | 3/1993 | Okada et al. | |
| 5,192,816 | A | 3/1993 | Iizuka | |
| 5,236,362 | A | 8/1993 | Cohen et al. | |
| 5,275,562 | A | 1/1994 | McSpadden | |
| 5,306,338 | A | 4/1994 | Tsunekawa | |
| 5,326,263 | A | 7/1994 | Weissman | 433/224 |
| 5,338,773 | A | 8/1994 | Lu et al. | 523/116 |
| 5,367,002 | A | 11/1994 | Huang et al. | |
| 5,520,725 | A | 5/1996 | Kato et al. | |
| RE35,264 | E | 6/1996 | Bennett | 433/220 |
| 5,540,766 | A | 7/1996 | Castellani | 106/35 |
| 5,548,002 | A | 8/1996 | Schwabe et al. | |
| 5,621,119 | A | 4/1997 | Podszun et al. | 549/229 |
| 5,624,976 | A | 4/1997 | Klee | |
| 5,681,872 | A | 10/1997 | Erbe | 523/114 |
| 5,763,622 | A | 6/1998 | Podszun et al. | 549/229 |
| 5,859,089 | A | 1/1999 | Qian | |
| 5,877,232 | A | 3/1999 | Storch et al. | |
| 5,908,879 | A | 6/1999 | Kawashima et al. | |
| 5,914,356 | A | 6/1999 | Erbe | 523/114 |
| 5,925,179 | A | 7/1999 | Mannschedel | 106/35 |
| 5,964,592 | A | 10/1999 | Hites et al. | 433/221 |
| 6,133,339 | A | 10/2000 | Xie et al. | |
| 6,183,253 | B1 | 2/2001 | Billet et al. | 433/81 |
| 6,217,644 | B1 | 4/2001 | Matsunae et al. | |
| 6,224,378 | B1 | 5/2001 | Valdes et al. | |
| 6,353,041 | B1 | 3/2002 | Qian | |
| 6,371,763 | B1 | 4/2002 | Sicurelli, Jr. et al. | 433/220 |
| 6,455,608 | B1 | 9/2002 | Jia et al. | |
| 6,472,454 | B1 | 10/2002 | Qian | |
| 6,500,004 | B2 | 12/2002 | Jensen et al. | 433/228.1 |
| 6,512,068 | B1 | 1/2003 | Nakatsuka | |
| 6,534,121 | B1 | 3/2003 | Newton et al. | 427/142 |
| 6,638,069 | B2 | 10/2003 | Hagenbuch et al. | 433/194 |
| 6,729,879 | B2 * | 5/2004 | Allred et al. | 433/226 |
| 6,787,584 | B2 | 9/2004 | Jia et al. | |
| 6,986,662 | B2 | 1/2006 | Haschke | |
| 2002/0025506 | A1 | 2/2002 | Hagenbuch et al. | 433/201.1 |
| 2002/0045678 | A1 | 4/2002 | Lopez et al. | |
| 2002/0120033 | A1 | 8/2002 | Jia et al. | |
| 2003/0105433 | A1 | 6/2003 | Ruben | |
| 2003/0134933 | A1 | 7/2003 | Jia et al. | |
| 2003/0148247 | A1 | 8/2003 | Sicurelli, Jr. et al. | 433/220 |
| 2003/0180691 | A1 * | 9/2003 | Hamer et al. | 433/217.1 |
| 2003/0194682 | A1 | 10/2003 | Jensen et al. | 433/224 |
| 2004/0137404 | A1 | 7/2004 | Koch et al. | 433/81 |
| 2004/0202986 | A1 * | 10/2004 | Haschke | 433/224 |
| 2004/0249015 | A1 | 12/2004 | Jia et al. | |
| 2005/0196726 | A1 * | 9/2005 | Fischer | 433/224 |

FOREIGN PATENT DOCUMENTS

| | | |
|---|---|---|
| JP | 60-45510 | 3/1985 |
| JP | 61-151104 | 7/1986 |
| JP | 61-176506 | 8/1986 |
| JP | 63-162769 | 7/1988 |
| JP | 70-82115 | 3/1995 |
| JP | 80-99811 | 4/1996 |
| JP | 90-25208 | 1/1997 |

OTHER PUBLICATIONS

Chana, H., et al., Degradation of a silver point in association with endodontic infection; Int. Endod J., vol. 31(2), pp. 141-146 (1998).

Musikant, B.L., et al., Simplified Obturation of Tapered Canal Preparations; Compend. Contin. Educ. Dent., vol. 19(11), pp. 1152-1155 (1998).

Musikant, B.L., et al., Report of a Simplified Endodontic Technique; Compend. Contin. Educ. Dent., vol. 20(11), pp. 1088-1090, 1092-1094 (1999).

Seidman, D., A General Dentist's Viewpoint of Two New Endodontic Techniques; Compend. Contin. Educ. Dent., vol. 20(10), pp. 921-924, 926, 928 passim; quiz 934 (1999).

Musikant, B.L., et al., The Evolution of Instrumentation and Obturation Leading to a Simplifed Approach; Compend. Contin. Educ. Dent., vol. 21(11), pp. 980-986, 998, 990 (2000).

Office action dated Mar. 20, 2008 cited in related U.S. Appl. No. 11/109,424.

Office action dated Mar. 8, 2007 cited in U.S. Appl. No. 10/843,654.

Notice of Allowance dated Sep. 25, 2007 cited in related U.S. Appl. No. 10/843,654.

Office Action dated Aug. 26, 2008 from U.S. Appl. No. 11/109,424.

Office Action dated Oct. 16, 2008 from U.S. Appl. No. 11/232,062.

* cited by examiner

COMPOSITIONS, KITS AND METHODS FOR INITIATING OR ACCELERATING CURING OF ENDODONTIC FILLER OR SEALER COMPOSITIONS PLACED ON A ROOT CANAL

Matter enclosed in heavy brackets [ ] appears in the original patent but forms no part of this reissue specification; matter printed in italics indicates the additions made by reissue.

CROSS-REFERENCE TO RELATED APPLICATION

N/A

BACKGROUND OF THE INVENTION

1. The Field of the Invention

The present invention relates to concentrated curing compositions for use in initiating or accelerating curing endodontic sealer and filler compositions placed in a person's root canal. In addition, the invention relates to kits that include a microdose container filled with a concentrated curing composition used to coat or impregnate a dental tool for use in initiating or accelerating curing of an endodontic sealer or filler composition.

2. The Related Technology

In an endodontic root canal procedure, the root canal is typically cleaned using special root canal tools and irrigation devices. Following such a root canal procedure, it is important to fill and seal the evacuated root canal to preserve the dead tooth from further decay that might compromise the integrity of the tooth and cause infection. In a typical procedure, one or more soft, resilient, needle-like inserts known as "gutta percha" cones or points are inserted in each root canal branch to at least partially seal and fill the root canal.

The term "gutta percha" refers to a rubbery material derived from natural rubber and typically blended with zinc oxide. This particular rubbery material is preferred because it is compressible, flexible and relatively soft so that it can be used to fill voids within the exposed root canal. The gutta percha cones are typically impregnated with other materials such as radiopaque solids, zinc oxide, for its medicinal properties, and other passive or active ingredients as desired.

Filling a root canal with gutta percha often requires inserting more than one gutta percha point or cone. Most root canals are narrow at the apical end and widen as they move up through the tooth. The first gutta percha point or cone is used to seal the apex and is often referred to as the master cone. Following placement of the master cone, additional gutta percha points can be added to fill the increasingly larger void of the root canal.

Experience has shown that it is impossible to completely seal a root canal using gutta percha alone. To further seal the root canal, flowable materials, such as sealing resins, are inserted into the root canal along with the gutta percha points. One feature of most sealing resins is the need to harden or cure the resin. The sealing resin remains in a liquid state until polymerized by an initiator or curing agent. Because root canals are deep and narrow, photocuring a resin deep within the root canal is not possible. A chemical curing agent must be employed. The curing agent is typically mixed with the resin just prior to inserting the resin in the root canal, thereby giving the practitioner the greatest amount of time to work before the resin hardens.

One disadvantage of chemically curable resins is that once chemical curing begins the reaction cannot be easily stopped or inhibited. Thus, a practitioner has only a limited time to work with the material once hardening begins. In theory, this window of time can be lengthened or shorted in advance by selecting the amount or type of curing agent that is mixed with the curable resin. If the time is lengthened, the hardening step may take an undesirably long amount of time once the resin is placed in the tooth. If the time is shorted, the practitioner may be rushed if the procedure turns out to be more difficult than anticipated. Thus, while the cure time can be modified, at least in theory, before the procedure begins, once curing has been initiated, curing will proceed within whatever time frame is dictated by the curing agent. Depending on the temperature, extent of mixing, and other variable factors, the actual window of time in which the resin will cure may be unpredictable.

This inability to modify cure times once curing has been initiated can make certain steps of a root canal procedure difficult or impossible. For example, a practitioner may not have sufficient time to take an X-ray to determine whether the sealing material has successfully filled the entire root canal, including lateral canals and/or whether the gutta percha points have been properly positioned. Alternatively, the curing process may take too much time, thus wasting the patient's and the practitioner's time or making it necessary for the patient to return for a follow up procedure after the resin has fully hardened.

Therefore, what is needed are compositions, kits and methods that can be employed to reliably cure a curable resin placed within a person's root canal while giving the practitioner flexibility to increase or decrease the time the practitioner has to work with the resin while carrying out the dental filling procedure.

BRIEF SUMMARY OF THE INVENTION

The present invention overcomes the above mentioned problems in the prior art by providing curing compositions, kits and methods that allow a practitioner to control the timing and/or extent of the curing of an endodontic filler or sealer composition within a person's root canal. The curing composition is provided in concentrated form so that only a small quantity of the curing composition is required to initiate curing, which typically involves free radical polymerization and/or cross linking of one or more curable resins contained within the filler or sealer composition. The curable resins may include monomers, dimers, trimers, oligomers or other polymerizable units having ethylenically unsaturated groups (e.g., acrylic acid, methacrylic acid, or esters thereof).

In order to initiate and/or accelerate curing of an endodontic filler or sealer composition placed within a root canal, a suitably sized implement, such as an endodontic point or dental tool, is first coated or impregnated with the curable composition and then placed in the root canal containing the filler or sealer composition. According to one embodiment, coating or impregnating the implement is performed by the dental practitioner just prior to inserting the implement into the root canal. In one embodiment, the practitioner dips the implement in a vial containing a curing composition in concentrated form (e.g., a curing agent in a solvent or other carrier liquid). Because curing agents can be toxic, the concentrated curing composition is advantageously pre-packaged in a microdose container.

In another embodiment, the curing agent may be precoated on or impregnated within the implement, thereby forming an activating implement (e.g., endodontic point or dental tool). When the activating endodontic point or dental tool is placed in contact with a sealer or filler composition in a root canal, the endodontic point or dental tool initiates or accelerates polymerization of the sealer or filling material. The amount of curing agent pre-coated on or impregnated within the implement will typically be such that a desired level of curing will be attained (e.g., partial or total curing). Nevertheless, it is not so much the amount of curing agent but when the curing agent is first contacted with the filler or sealing composition within the root canal that is the main determining factor regarding the timing and/or extent of curing.

The curing agent can be any one of a number of components used to cure sealer or filler compositions. In an exemplary embodiment, the curing agent comprises one or more amines that initiate or accelerate polymerization of the sealer or filling composition by destabilizing a peroxide contained within the sealer or filler composition. The destabilized peroxide can then initiate free radical polymerization (e.g., of an acrylate- or methacrylate-based sealer or filler composition). Alternatively, the curing agent may comprise one or more peroxides that are initially stable when coated or impregnated onto the implement but which are destabilized by one or more amines contained within the sealer or filler composition. Other polymerizable sealer or filler compositions that can be initiated using an appropriate curing agent coated on or impregnated within an implement, such as an endodontic point or dental tool, include epoxy- or cationic-based compositions.

A kit for use in initiating or accelerating curing of an endodontic filler or sealer composition may include one or more microdose containers, each including an appropriate quantity and/or concentration of curing composition. Because the curing agent can be toxic, particularly in the case of amines, a microdose container containing a very small quantity of the curing composition can be provided. By way of example, microdose containers within the scope of the invention may contain from about 0.01 ml to about 1 ml of the curing composition, preferably from about 0.05 ml to about 0.5 ml, and more preferably from about 0.075 ml to about 0.25 ml. According to one embodiment, the microdose container contains about 0.1-0.15 ml of the curing composition.

It is within the scope of the invention to provide curing compositions having differing concentrations and/or amounts of curing agent in order to provide different cure times. In this embodiment, a dental practitioner can select an appropriate composition from the kit and dip an implement or substrate into the curing agent composition so as to form the activating implement or substrate just prior to use. The dental practitioner can control the cure time by selecting the proper curing agent composition. The kit may optionally include one or more implements (e.g., rigid elongated devices, such as plastic or metal rods) that may be coated and/or impregnated with the curing composition prior to inserting an implement within a filler or sealer composition within a root canal to initiate and/or accelerate curing thereof.

Alternatively, kits within the scope of the invention may include one or more endodontic filler or sealer compositions and one or more microdose containers that contain appropriate amounts and/or concentrations of curing composition (e.g., to provide single or variable cure times). The endodontic filler or sealer composition may be pre-packaged within an appropriate container, such as a syringe. One or more syringe tips containing a cannula sufficiently narrow to be placed within a root canal may be provided with the kit. The filler or sealer compositions may include part of a curing system complementary to the curing composition. They may also comprise two-part chemical cure compositions that include an amount of curing agent when mixed so that only slow curing occurs. The curing compositions are then used to merely accelerate rather than initiate curing. Such kits may also include one or more implements as previously discussed.

In an alternative embodiment, kits are provided that include a plurality of implements that are pre-coated or impregnated with a curing agent. In one embodiment, the implements may include different amounts of curing agent so as to provide different cure times. The kit may include endodontic cones that are intended to be sequentially placed into a root canal during a filling or sealing procedure. In such case, one or more cones that are to be placed first may include an amount of curing agent that only initiates slow curing of the filler or sealer composition. One or more cones that are to be placed later may include an amount of curing agent that more rapidly cures the filler or sealer composition.

For example, a kit containing one or more master cones and one or more accessory cones can be used to select when or how fast to initiate the curing process. According to one embodiment, the master cone may be treated with a curing agent to initiate either slow or fast curing. Accessory cones designed to be placed into a root canal after the master cone can be treated with a curing agent. In the case where the master cone is treated to initiate slower curing one or more accessory cones can be used to initiate faster curing. In some cases only the accessory cones will be treated such that the master cone does not itself initiate curing.

The present invention also includes methods for performing an endodontic procedure. The methods of the present invention include performing a root canal on the tooth of a person or animal to prepare the root canal for a sealer or filling composition, placing a sealer or filler composition in the root canal, and initiating or accelerating the polymerization of the filler or sealer composition by placing an activating endodontic point or dental tool in contact with the sealer or filler composition. The method may employ any of the inventive compositions and/or kits disclosed herein to provide a desired rate or extent of curing of the filler or sealer compositions positioned within the root canal.

The compositions, kits and methods of the present invention allow a practitioner to better control when a sealer or filler composition is cured during the endodontic procedure and the time within which curing will occur. Using the present invention, a practitioner can prepare and place a curable sealer or filling material in the root canal and wait for a desired amount of time before initiating or causing complete polymerization and/or cross linking. The practitioner can control the timing of curing by selecting when to place the activating endodontic point or dental tool in the sealer or filler material. Furthermore, by controlling the concentration and/or amount of curing agent on or within the endodontic point, dental tool or other implement, the rate of polymerization can also be controlled. Unlike light curing alone, which may only cure an upper portion of the sealer or filler material, the present invention allows for complete curing along the entire root canal.

Providing the practitioner with better control over the timing and duration of curing reduces the time and expense of an endodontic procedure and can improve the quality of the procedure. One advantage of controlling cure timing is that the practitioner can choose to perform a step, such as taking X-rays, to determine proper placement of the filler or sealer material and/or endodontic point (e.g., a master cone). Because the practitioner can select when to cause curing of the sealer or filler material, the practitioner can cause very rapid curing after performing any necessary prep work. This allows subsequent procedures, such as restorative procedures, to be performed immediately following the sealing or filling procedure. For example, this feature can allow a patient to receive a root canal and a restorative post procedure in a single office visit.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

Figure 1:
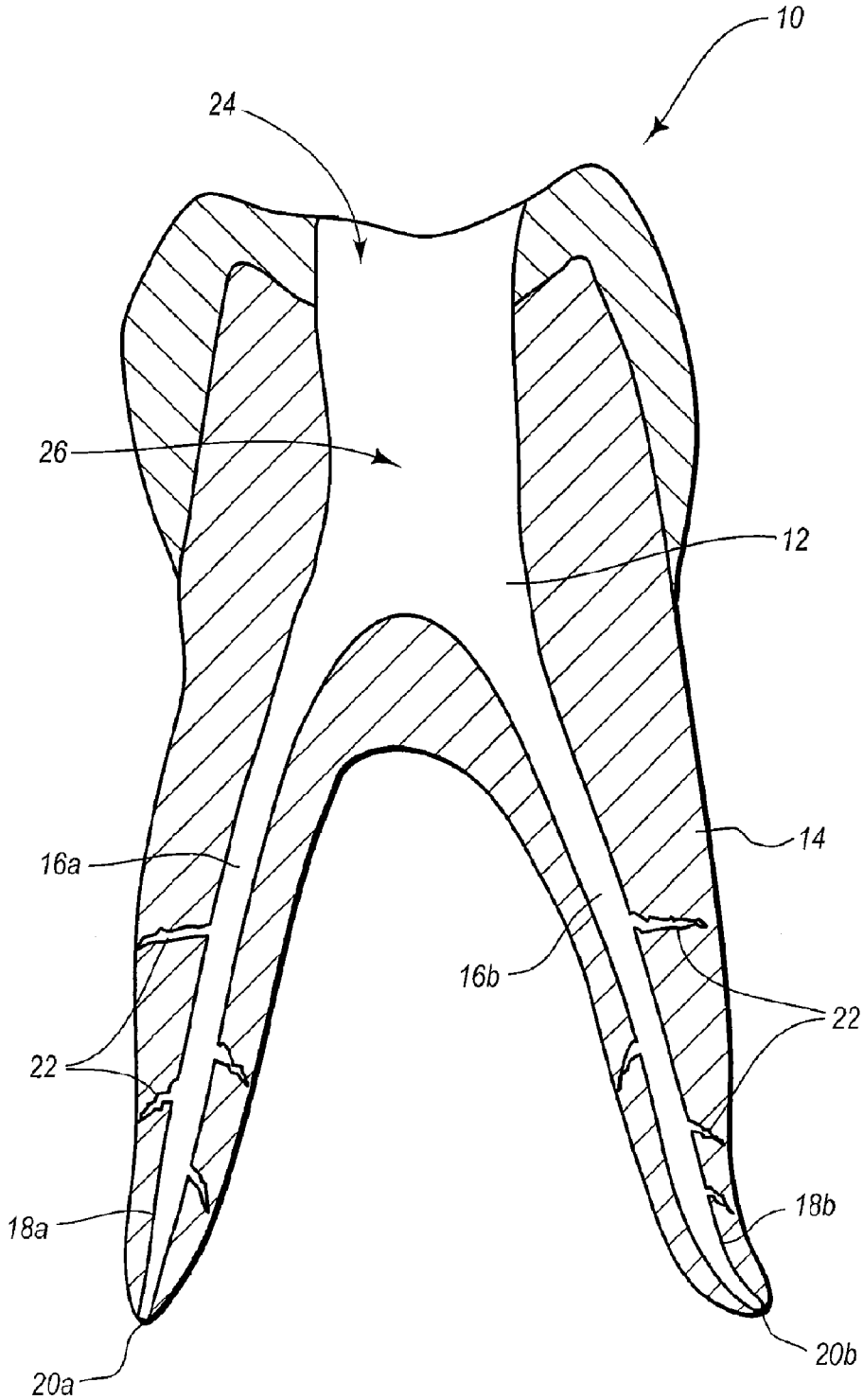
FIG. 1 illustrates an exemplary tooth with its root prepared in an endodontic procedure for sealing and filling according to an exemplary embodiment of the present invention.

The invention encompasses compositions, kits and methods used to control the timing and/or extent of curing sealer and filler compositions placed in a root canal during an endodontic procedure. Curing compositions include a curing agent in concentrated form. An implement such as an endodontic point or dental tool can be coated or impregnated with the curing composition and then inserted into a filler or sealer composition positioned within a root canal. Alternatively, the endodontic point or dental instrument may be pre-coated or impregnated with a curing agent to form an activating implement. When contacted with a sealer or filler composition, the curing agent initiates or accelerates polymerization and/or cross linking of the sealer or filler composition. The timing when curing of the endodontic filler or sealer composition can be controlled by selecting when to contact the curable composition with the curing agent. Furthermore, the cure time can be further controlled by controlling the concentration and/or amount of curing agent that is coated on or impregnated within the implement.

According to one embodiment, the curing composition can be used to initiate curing of a filler or sealer composition placed in a root canal. In another embodiment, the curing composition can be used to accelerate curing of a filler or sealer composition placed in a root canal that has already begun to cure but which is curing slowly to provide adequate time for the endodontist to perform desired and/or necessary procedures prior to final cure.

I. CURING AGENTS AND COMPOSITIONS

Curing compositions within the scope of the invention preferably contain one or more curing agents in concentrated form. That allows a small amount of the curing composition to quickly initiate and/or accelerate curing of a filler or sealer composition within a root canal.

An appropriate curing agent is selected to initiate or accelerate polymerization of the particular sealer or filler composition being used to fill and/or seal the root canal. The curing agent may be one part of a curing system that is capable of polymerizing the sealer or filler composition. Generally, any component of a curing system can be used as the curing agent so long as that compound can initiate and/or accelerate polymerization of the sealer or filler composition. The curing agent may be selected to initiate curing of any polymerizable sealant or filler composition, including but not limited to, acrylic acid- and/or methacrylic acid-based compositions, acrylate- and/or methacrylate-based compositions, epoxy-based compositions, and cationic-based compositions.

The curing agent can be coated on or impregnated within an implement, such as an endodontic cone or dental tool, either prior to or just before use. When the coated or impregnated substrate or implement is placed in contact with a sealer or filler composition, the curing agent causes polymerization and/or cross linking of the sealer or filler composition.

The curing agent of the present invention can be a chemical initiator or it can be an additive that works with a chemical initiator to initiate or accelerate polymerization of the sealer or filler composition. Chemical initiators are compounds that induce polymerization and/or cross linking (e.g., free radical polymerization and/or cross linking) of the polymerizable material. Additives are compounds that react with initiators in order to cause the initiators to induce polymerization and/or cross linking.

Examples of chemical initiators that induce free radical polymerization and/or cross linking include a wide range of peroxides, other per compounds, and other free radical generators. Exemplary peroxides include benzoyl peroxide, 2-butanone peroxide, lauroyl peroxide and tert-butyl peroxide. Peroxides are typically stable, or can be made stable, until it is desired to initiate free radical polymerization and/or cross linking. An additive is used to destabilize the peroxide, causing free radicals to be generated that are able to then induce polymerization and/or cross linking of the curable composition (e.g., by means of free radical induced polymerization and/or cross linking of ethylenically unsaturated groups contained in the polymerizable units).

Examples of additives that can be used to destabilize peroxide initiators include a wide variety of amines (i.e., amino compounds). Examples of amino compounds include dimethylamino ethyl methacrylate, triethyl amine, 2-dimethylamino ethanol, diethylamino ethyl methacrylate, trihexyl amine, N,N-dimethyl-p-toluidine (also referred to as DMPT), N-methylethanolamine, 2,2'(p-tolyimino)diethanol (also referred to as P-TIDE), and derivatives thereof.

According to one embodiment, the curing composition applied to a substrate or implement and then inserted into the curable resin to initiate or accelerate curing comprises an amine or other additive that is able to react with and destabilize a peroxide or other initiator that is already mixed within the curable resin within the root canal. In another embodiment, the curing composition applied to a substrate or implement and then inserted into the curable resin to initiate or accelerate curing comprises a peroxide or other initiator that is able to react with and become destabilized by an amine or other additive that is already mixed within the curable resin within the root canal.

The curing agent, whether an initiator or additive, is preferably contained in high concentration within the curing composition, typically as a solution or suspension together with an appropriate solvent or carrier liquid. This allows a relatively small amount of the curing composition coated on or impregnated within an implement to initiate or accelerate curing of an endodontic filler or sealer composition placed within a root canal. Accordingly, the curing agent may have a concentration in a range of about 25% to 100% by weight of the curing composition, preferably from about 35% to about 75% by weight, and most preferably from about 45% to about 55% by weight.

Any appropriate solvent or other carrier liquid can be mixed with the curing agent to yield a curing composition having a desired concentration of curing agent. A solvent or other carrier is typically selected that does not itself react with the curing agent. The solvent may be non-reactive or it may itself be capable of polymerizing. The curing composition is preferably fluid and non-viscous to facilitate fast diffusion of the curing composition into the curable composition. Examples of non-polymerizable solvents and other carriers that may be used to formulate curing compositions within the scope of the invention include water, methanol, ethanol, isopropyl alcohol, propylene glycol, 1,3-propanediol, glycerin, polyethylene glycol, polypropylene glycol, acetone, toluene, xylene, ethyl acetate, DMSO, DMF, and acetonitrile. An examples of a polymerizable solvent or carrier is triethylene glycol dimethacrylate (TEG-DMA).

As discussed more fully below, the curing composition can be pre-coated on or impregnated within an implement, such as an endodontic cone, to form an activating dental implement or substrate. Depending on the chemical make up of the implement, the curing composition that is pre-coated on or impregnated in the implement may simply include a curing agent and solvent or other carrier liquid, as discussed above. Alternatively, the curing composition may further include one or more polymerizable materials in order to improve adhesion of the curing agent to the substrate, particularly in the case where the substrate is hydrophobic, such as gutta percha, or otherwise has a tendency to repel the curing agent.

The curing agent may optionally include a preservative such as a free-radical scavenger, which is especially advantageous in the case where the solvent or carrier is capable of free radical polymerization. An example of a free radical scavenger that can be used to prevent premature polymerization of a polymerizable solvent or carrier is butylated hydroxytoluene (BHT). Another is butylated hydroxyanisole (BHA).

II. ACTIVATING IMPLEMENTS

In a preferred embodiment, the activating substrate or implement of the present invention is an endodontic point. However, almost any material that can be sized and configured for insertion into a root canal of a person can be used as the substrate for the present invention. FIG. 1 depicts a tooth 10 that has been subjected to a root canal procedure such that a substrate can be inserted therein. The tooth 10 includes a root canal 12 in tooth root 14. Root canal 12 includes root canal portions 16a and 16b. Root canal portions 16a and 16b terminate at apexes 18a and 18b, respectively to create root openings 20a and 20b. Lateral canals 22 extend into root 14 from root canal 12. An opening 24 in the crown of the tooth provides access to root canal 12.

The substrate of the present invention is sized and configured to be inserted through opening 24 and into root canal 12. In one embodiment, the substrate is configured to be, inserted into the pulp chamber 26. Alternatively, the substrate of the present invention can be sized and configured to be at least partially placed in the root canal portions 16a or 16b.

Typically, substrates that can be inserted into root canal 12 have a diameter between about 0.1 and 1.1 mm for human teeth. Animals however, can have much larger root canals, such as up to about 20 mm.

Figure 2:
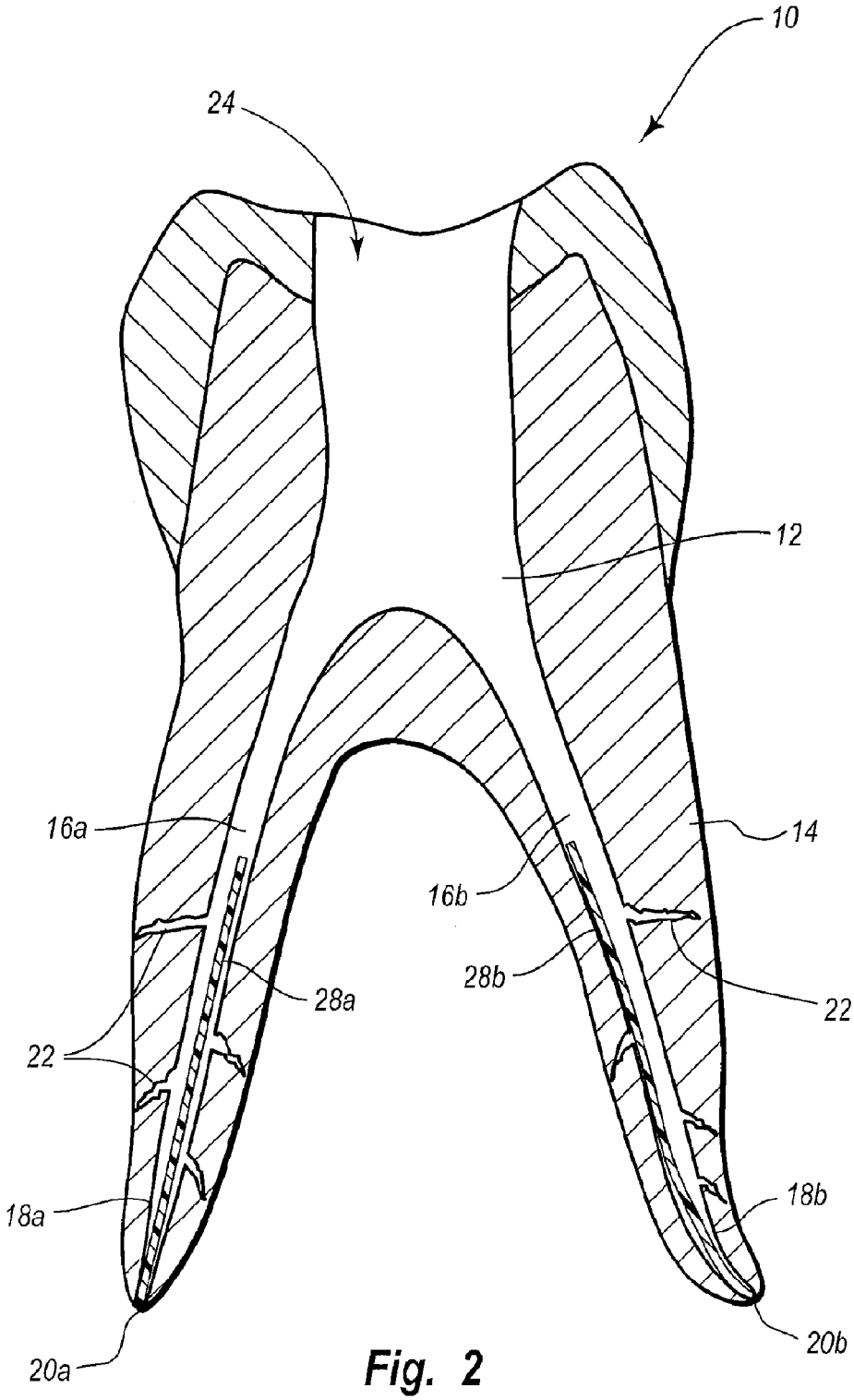
FIG. 2 illustrates placement of an endodontic point in the apex of the tooth of FIG. 1.

In an exemplary embodiment, the substrate of the present invention is an endodontic point. FIG. 2 shows endodontic points 28a and 28b inserted into apexes 18a and 18b respectively. As discussed below, endodontic points 28a and 28b can be coated or impregnated with a curing agent according to the present invention. Endodontic points 28a and 28b can be made of gutta percha and are used for their typical benefit, which is to plug or seal root openings 20a and 20b in root canals 16a and 16b respectively.

Using endodontic points 28a and 28b as a substrate according to the present invention has the added benefit of not requiring additional materials or tools to be placed in the root canal. This aspect of the invention can be particularly beneficial where the substrate needs to be placed near apex 18 since root canal 16a and 16b can be very narrow at the apex.

Endodontic points 28a and 28b shown in FIG. 2 are master points and can be used as a substrate according to the present invention. However, as shown in FIG. 5, accessory cones such as endodontic points 38a and 38b can also be used as a substrate. In existing endodontic procedures, accessory cones are typically used to seal lateral canals 22, where the master cones are used to plug the opening in the apex. In the case where accessory cones are used, only the accessory cones are activating so that curing is not initiated or accelerated until placement of the accessory cones. This allows a dentist or endodontist to take one or more X-rays to ensure proper placement of the filler or sealer and the master cone(s) prior to initiating or accelerating curing. It is also within the scope of the invention to use a master cone that is treated to initiate either fast or slow curing.

In an alternative embodiment, a dental tool or other device can be used as a substrate. For example, syringe 30, shown in FIG. 3 (e.g., an outer surface of cannula 34), can be used as a substrate in addition to being used as a tool to inject a sealer composition into the root canal. Alternatively, the substrate can be another dental tool such as an endodontic file (not shown) or thin piece of plastic or other material (not shown) so long as the substrate is sized and configured to be placed into at least a portion of a root canal. One of skill in the art would readily be able to select an appropriate endodontic file or construct a narrow cross-sectioned implement that can fit at least partially into a root canal.

In an exemplary embodiment, activating implements, such as endodontic points and dental tools, are made by dipping the implement or substrate into a composition that includes the curing agent. In one embodiment, the curing agent is mixed with one or more of a polymer or a solvent, and the substrate is dipped into the polymer or solvent. By mixing the curing agent at least one of a polymer or solvent, the polymer or solvent can be used as a carrier for coating or impregnating the substrate. In another embodiment, the substrate is dipped directly into pure curing agent. However, in the case where only a minute quantity of curing agent is able to initiate or accelerate curing, it will be preferable to include a solution of curing agent and solvent.

While any coating or impregnation method can be used to apply the curing agent to the substrate, using a carrier can be particularly effective. First, using a carrier can provide an appropriate distribution of the curing agent over the substrate. For example, where a dental tool such as a metal tool is being used, a polymeric mixture can be used that has a viscous or adhesive property that causes the polymeric mixture to adhere to the dental tool. In another embodiment, where a gutta percha point is used, a solvent can be used that can penetrate the gutta percha and impregnate it. Nevertheless, dental tools and gutta percha endodontic points can be coated using a polymeric material instead of, or in addition to, a solvent.

A second advantage of using a carrier such as a solvent or polymer to deliver the curing agent is that mixing the curing agent allows the concentration of the curing agent to be controlled. Typically, the cure time depends on the concentration of the curing agent in the sealer or filler composition. This is accomplished by making the curing agent the limiting reagent or choosing a curing agent that can accelerate the reaction. In one exemplary embodiment, the curing agent is an amine that destabilizes a peroxide in the sealer or filler material. The concentration of the amine in the sealer or filler material determines in large part the magnitude of the cure time.

Coating or impregnating the substrate by dipping the substrate directly in a curing agent liquid such as P-TIDE or DMPT results in cure times of less than about 30 seconds. By mixing the curing agent with a carrier such as a polymer or a solvent, the cure time can be extended to any desired amount of time.

Suitable polymers useful as a carrier for the curing agent include acrylate based polymers such as methacrylates and di-acrylates. In an exemplary embodiment, the polymers used as a carrier for the curing agent are similar or identical to the polymers used in the sealer or filling material. A solvent is typically used to impregnate an endodontic point or dental tool. An example of a solvent suitable for using in the present invention is toluene.

In an exemplary embodiment, the curing agent is an amine that is included in a polymeric material and the concentration of amine is between about 0.1 and about 35% of the polymeric mixture. The concentration of curing agent will depend on the curing agent selected. For example, P-TIDE is typically used in a range of between about 5% and 35%, and more preferably in a range of about 20%-25% of the coating. A coating having P-TIDE in a concentration of about 20% to about 25% causes the sealer or filler material in the root canal to cure in about 2-4 minutes.

In another example, DMPT is used with the solvent toluene, preferably in a concentration of about 0.1% to about 20%, and more preferably in a concentration of about 1%-2%. DMPT in a concentration of about 2% in toluene and impregnated on an endodontic point causes curing in about 8 minutes when placed in a sealer or filler in a root canal.

Those skilled in the art will recognize that there are many combinations of initiators, peroxides, amines, and other compounds that work with many different curable resins and that these different compounds can be used as curing agents to carry out the invention described herein. Those skilled in the art are also familiar with cure times for various concentrations of curing agent in curable resins. Thus, while various examples have been provided for purposes of illustrating the invention, those skilled in the art can easily adapt these teachings to numerous curable resins and curing systems that are available for sealing or filling root canals.

The carrier compounds described above, including polymers and solvents are examples of carrier compound means for coating or impregnating a substrate with a curing agent.

When making an activating endodontic point or dental tool according to the present invention, any portion of the substrate can be coated or impregnated. Typically, for an endodontic point, the entire length of the point is coated or impregnated since gutta percha points may be completely inserted into the root canal. A dental tool on the other hand is typically only partially inserted into the root canal. Thus, only a portion of the dental tool is typically coated or impregnated so as to not waste the active agent.

The activating endodontic points and dental tools of the present invention can be coated or impregnated during manufacture. Alternatively, a curing agent composition can be provided to the dental practitioner who then mixes and/or dips a substrate in the curing agent composition to prepare the activating endodontic point or dental tool just before use.

III. CURABLE FILLING AND SEALING COMPOSITIONS

Figure 3:
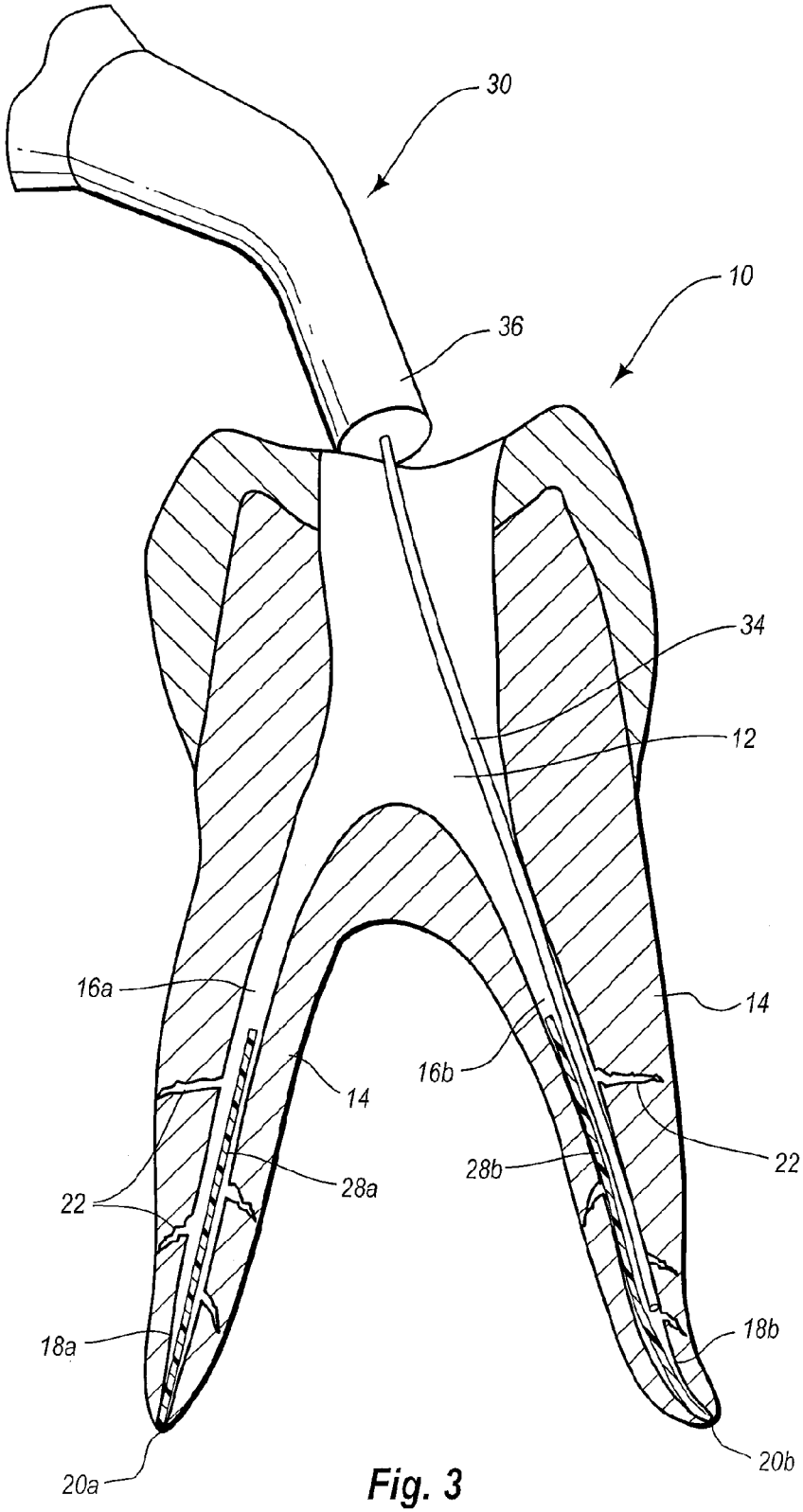
FIG. 3 illustrates filling the root canal of the tooth of FIG. 2 with an endodontic sealer or filler composition.
Figure 4:
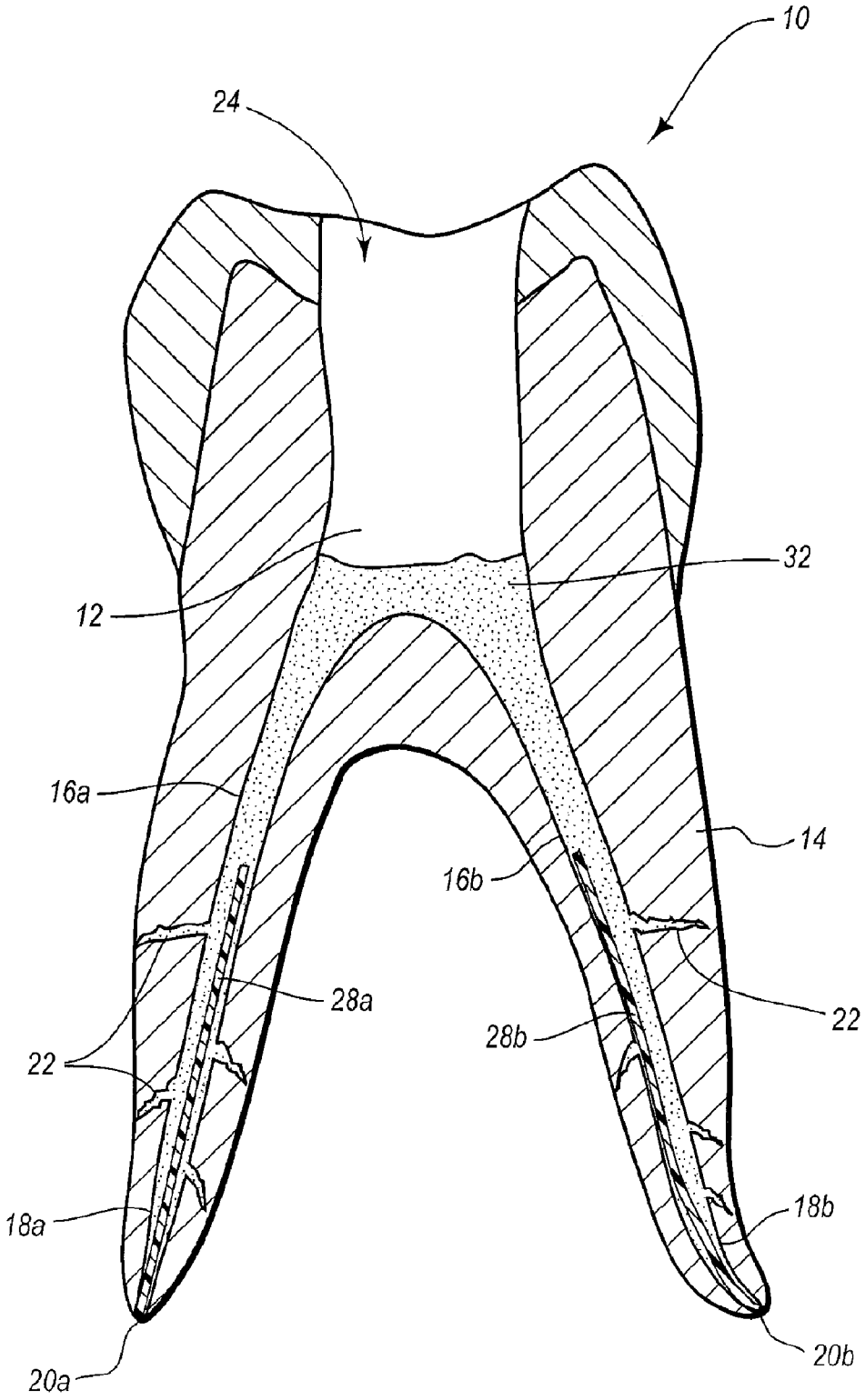
FIG. 4 illustrates the tooth of FIG. 2 partially filled with a sealer or filler composition.

The endodontic sealer and filler compositions used with the inventive curing compositions and activating implements or substrates according to the invention include at least one chemical curable resin material. The curable resin is initially in a liquid or shapeable form. As shown in FIGS. 3 and 4, sealer or filler composition 32 is placed in root canals 16a and 16b. Sealer or filler composition 32 fills root canals 16 such that root canals 16 and lateral canals 22 are sealed off from each other and opening 24. Sealing root canals 16 and lateral canals 22 help prevent bacteria and other microbes from entering root canal 12 or lateral canals 22 and spreading infection or decay within tooth root 14.

In general, any polymerizable material capable of sealing a root canal can be used with the present invention. Examples of suitable primary polymerizable resins include a wide range of acrylic acid- and methacrylic acid-containing compounds, acrylates, methacrylates, alkylhydroxy methacrylates, alkylamino methacrylates, epoxy-based compositions, cationic-based compositions, and derivatives thereof. More specific examples of polymerizable materials include glycidyl dimethacrylate, 2-hydroxy ethyl methacrylate, 3-hydroxy propyl methacrylate, 4-hydroxy butyl methacrylate, triethylene glycol dimethacrylate, and polyethylene glycol dimethacrylate. An example of an epoxy-based endodontic sealant resin that can be catalyzed using activating endodontic points or tools according to the invention is AH 26, available from Dentsply.

In one exemplary embodiment, the polymerizable resin includes an oxyphosphorus alkyl methacrylate, such as bis glycerol dimethacrylate phosphate. Examples of other oxyphosphorus alkyl methacrylates within the scope of the invention include bis 2-hydroxy ethyl methacrylate phosphate, phosphate ester of p-hydroxyphenyl methacrylamide, phosphate ester of 3-hydroxy propyl methacrylate, and phosphate ester of 4-hydroxy butyl methacrylate. The oxyphosphorus group increases the adhesiveness and water solubility (i.e., hydrophilicity) of the resulting resin.

One or more additional (or diluent) monomers can be added to achieve the desired properties of initial flowability, curability, and final cured strength and hardness. Diluent monomers suitable for use in the present invention include urethane dimethacrylate, p-hydroxyphenyl methacrylamide, butane diol dimethacrylate, and bisphenol-A-diglycidyl dimethacrylate ("Bis-GMA").

The primary polymerizable resins are preferably included in a concentration ranging from about 1% to about 90% by weight of the composition, more preferably from about 10% to about 80% by weight, and most preferably from, about 20% to about 70% by weight of the composition.

The diluent monomers may be included in amounts of up to about 95% by weight of the composition, preferably in a range from about 10% to about 80%, and more preferably in a range from about 30% to about 70% by weight of the composition.

The filler and sealer compositions may include other components or adjuvents as desired to yield compositions having desired properties. Examples include fillers, such as radiopaque fillers, and non-chemically triggered curing initiators that do not themselves initiate polymerization or cross linking absent application of an appropriate curing stimulus (e.g., light or heat). Thus, in addition to being chemical curable, the filler or sealer compositions may be heat curable, photo curable, dual curable, or use any other curing process or combination of curing processes to initiate or accelerate curing.

In the case of chemical and dual curable sealer or filler compositions, the curing system typically includes two or more parts that are initially kept separate but which are mixed together to initiate curing. In a conventional chemical or dual cure system, one part of the system includes constituents of the resin sealer or filling together with one part of the chemical cure system (e.g., one or more peroxide compounds), while another part includes constituents of the resin sealing with the other half of the chemical cure system (e.g., an amino compound). The present invention deviates from such systems in one of several ways. In a first embodiment, a single component chemical curable composition is provided that includes only one part of a two-part chemical cure system. The other part of the two-part chemical cure system is provided by the curing composition, as discussed above, and introduced into the curable composition in concentrated form by means of an implement coated or impregnated with the curing agent comprising the other part of the curing system. In this way, curing is not initiated until an activating implement coated or impregnated with the curing agent contacts with the curable composition.

Alternatively, curing of a chemical or dual cure composition may already have begun but can be accelerated using an activating implement. According to one embodiment, a two-part chemical cure composition is provided and mixed together prior to placement into the root canal, except that a deficient amount of one part of the curing system is provided so that only partial or slow curing of the composition occurs. Curing of the composition may thereafter be accelerated by introducing an additional quantity of the initially deficient part of the curing system (i.e., curing agent) by means of the activating implement or substrate.

The curable compositions may be cured in ways other than by chemical curing. For example, in one type of dual cure composition, a photoinitiator is included in order to permit photocuring of at least an upper or more exposed portion of the curable composition within a root canal. Examples of photoinitiators that may be used within the scope of the invention include camphor quinone, benzoin methyl ether, 2-hydroxy-2-methyl-1-phenyl-1-propanone, diphenyl 2,4,6-trimethylbenzoyl phosphine oxide, benzoin ethyl ether, benzophenone, 9,10-anthraquinone, and derivatives thereof.

When included, photoinitiators are preferably included in an amount in a range from about 0.05% to about 5% by weight of the composition, more preferably in a range from about 0.1% to about 2% by weight, and most preferably in a range from about 0.2% to about 1% by weight of the composition. In the case of a photocurable sealer or filling composition, the polymerizable resin is advantageously stable in the presence of the photoinitiator absent the application of radiant energy.

IV. METHODS OF USING CURING COMPOSITIONS AND ACTIVATING IMPLEMENTS TO CONTROL CURE TIME OF AN ENDODONTIC FILLER OR SEALER

The endodontic points and dental tools of the present invention can be advantageously used in an endodontic procedure to control the cure times of the endodontic sealer or filler composition. FIGS. 1-4 illustrate a tooth in various steps of an endodontic procedure.

As discussed above, FIG. 1 shows tooth 10 with root canal 12 that has been prepared using known endodontic techniques. In FIG. 2, master endodontic points 28a and 28b are placed in root openings 20a and 20b respectively. To ensure that endodontic points or cones 28a and 28b form a reliable seal within openings 20a and 20b, a procedure involving "tug back" is preferably performed. One of ordinary skill in the art of endodontics will know when there is sufficient tug back to confirm an adequate seal of the apexes 18a and 18b by master endodontic cones 28a and 28b. Sufficient tug back indicates that the fit between the gutta percha cone and the apex is sufficiently tight to adequately seal the apex and prevent flow of sealer or filling material into the surrounding bone tissue.

In a preferred method for placing a resinous sealer or filling material within a root canal, FIG. 3 depicts syringe 30 having a narrow diameter cannula 34 attached to tip 36 of syringe 30 used to insert sealer or filling material into root canal 12. Due to the narrow opening of the cannula 34, and because typical sealer or filling materials are often viscous, it can be advantageous for syringe 30 to be attached to a high pressure hydraulic injection system. Examples of high pressure hydraulic syringes or systems are set forth in U.S. Pat. No. 6,425,885, which is assigned to Ultradent, Inc. Examples of narrow cannulas sized for entry into a root canal are set forth in U.S. Pat. No. 6,079,979, which is assigned to Ultradent Products, Inc. For purposes of disclosing hydraulic pressurizing systems and cannulas sized to fit within a root canal, the foregoing patents are incorporated herein by reference.

The tip of the cannula 34 is initially placed within the root canal 12 near one of the apexes 18a or 18b and sealer or filling material 32 (FIG. 4) is injected into root canal 12. As the resinous material begins and continues to fill up the root canal portion 16b, the cannula 34 is slowly raised or withdrawn. This manner of filling the root canal 12 with resinous material minimizes or eliminates the formation of air pockets or bubbles as the resin is progressively placed within the root canal 12. This procedure greatly improves the ability of the resin to initially purge most or all of the air from within the root canal 12. As shown in FIG. 4, accessory points 38a and 38b are inserted into root canal 12 to seal the root and/or deliver sealing material 30. One or both accessory points 38a and 38b can be treated with a curing agent to initiate or accelerate curing.

In an alternative embodiment, the sealer or filler composition is placed in root canal 12 by first dipping the endodontic points in a resin and then inserting the point into the root canal. When the endodontic point is dipped, resin is coated thereon and is carried into the root canal with the endodontic point. In one embodiment, some or all of the sealer or filler composition is introduced into the root canal using a master cone. In addition, or alternatively, some or all of the sealer of filler composition can be introduced into the root canal using one or more accessory cones.

Some or all of the endodontic cones can be treated to initiate curing. In the case where the master cone is used to introduce the sealer or filler composition into the root canal, the accessory cones may be treated with a curing agent and used to initiate curing. In the case where the accessory cones are used to introduce the sealer or filler composition into the root canal, the master cone may be treated so as to initiate curing after insertion of the composition-laden accessory cone(s).

Controlling the curing time of an endodontic sealer or filling material according to the present invention is accomplished by either (i) selecting when to place an activating implement, such as endodontic point or dental tool, in the curable sealer or filling material, and/or (ii) selecting an activating endodontic point or dental tool with a predetermined amount or concentration of curing agent.

The first aspect of controlling curing according to the present invention enables a practitioner to delay curing of the sealer or filler composition by choosing when to place the activating implement in contact with the sealer or filler composition 32. In the exemplary embodiments illustrated in FIGS. 1-4, accessory endodontic points or cones 38a and 38b are used by the practitioner to control curing of the endodontic sealer or filler composition. In this embodiment, sealer or filler composition 32 contains little or no of the curing agent needed to initiate curing when it is placed in the root canal. In addition, the master endodontic cones 28a and 28b are not activating and therefore do not initiate or accelerate curing. Thus, the practitioner can have any amount of time to place the sealer or filler material 32. In addition, the practitioner has time to perform other desired procedures. For example, the practitioner can take X-rays of tooth 10 to determine whether the master endodontic points 28a and 28b have properly sealed the apex and/or whether the sealer or filler material has been properly placed in root canal 12 and/or lateral canals 22.

Figure 5A:
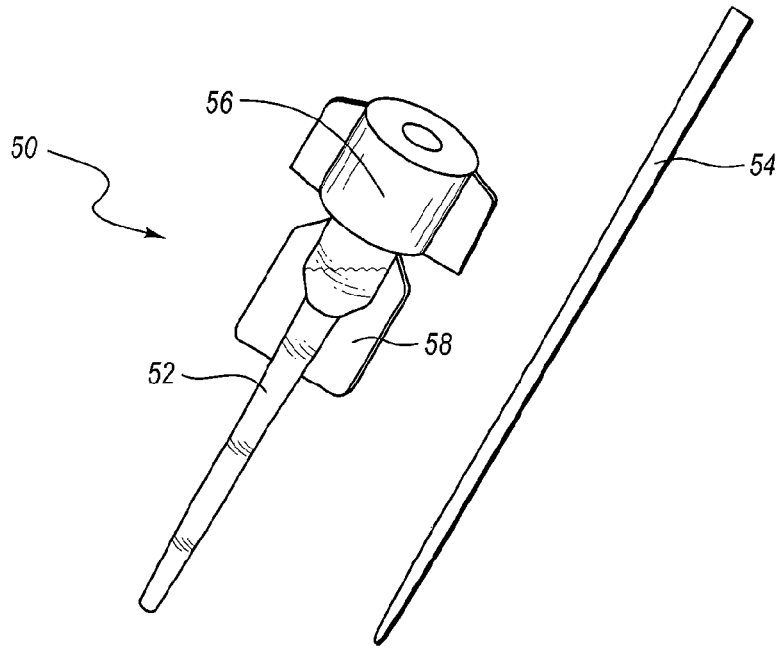
FIGS. 5A and 5B illustrate the act of dipping an endodontic cone into a microdose container that contains therein a microdose of a curing composition.
Figure 5B:
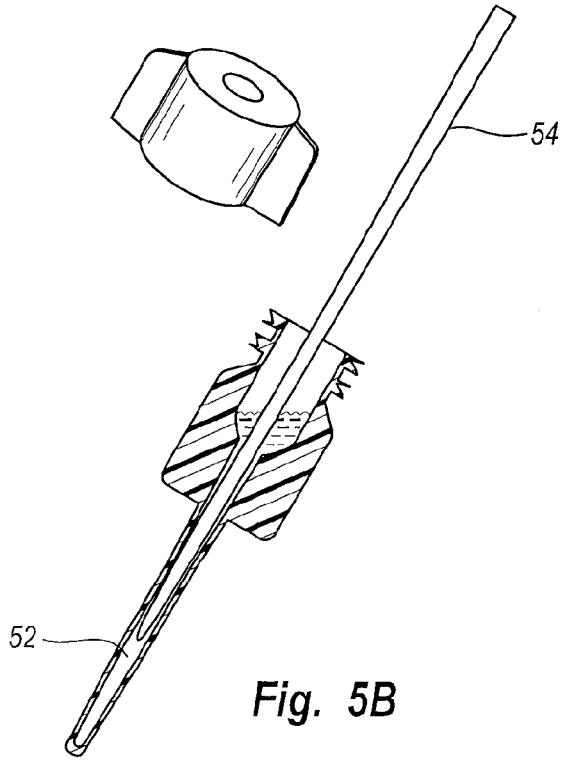

According to one embodiment, an activating implement is form in situ by dipping a substrate into a microdose container containing a small amount of a concentrated curing composition. An exemplary microdose container 50 is depicted in FIG. 5A. The container 50 includes an elongate chamber 52 that has an interior diameter that accommodates insertion therein of an endodontic cone 54 (e.g., gutta percha) or other similarly sized implement (not shown) that can be inserted into a root canal. A lid 56 is provided for initially sealing the curing composition prior to use. Wings 58 may be provided to enhance grip and control of the relatively small sized container 50 by the practitioner. The lid 56 may be a screw cap that is able to screw over corresponding threads of the container 50. As shown in FIG. 5B, the activating implement is formed by removing lid 56 and inserting endodontic cone 54 or other implement into the elongate chamber in order to coat the surface of the endodontic cone 54 or other implement with the curing composition.

Figure 6:
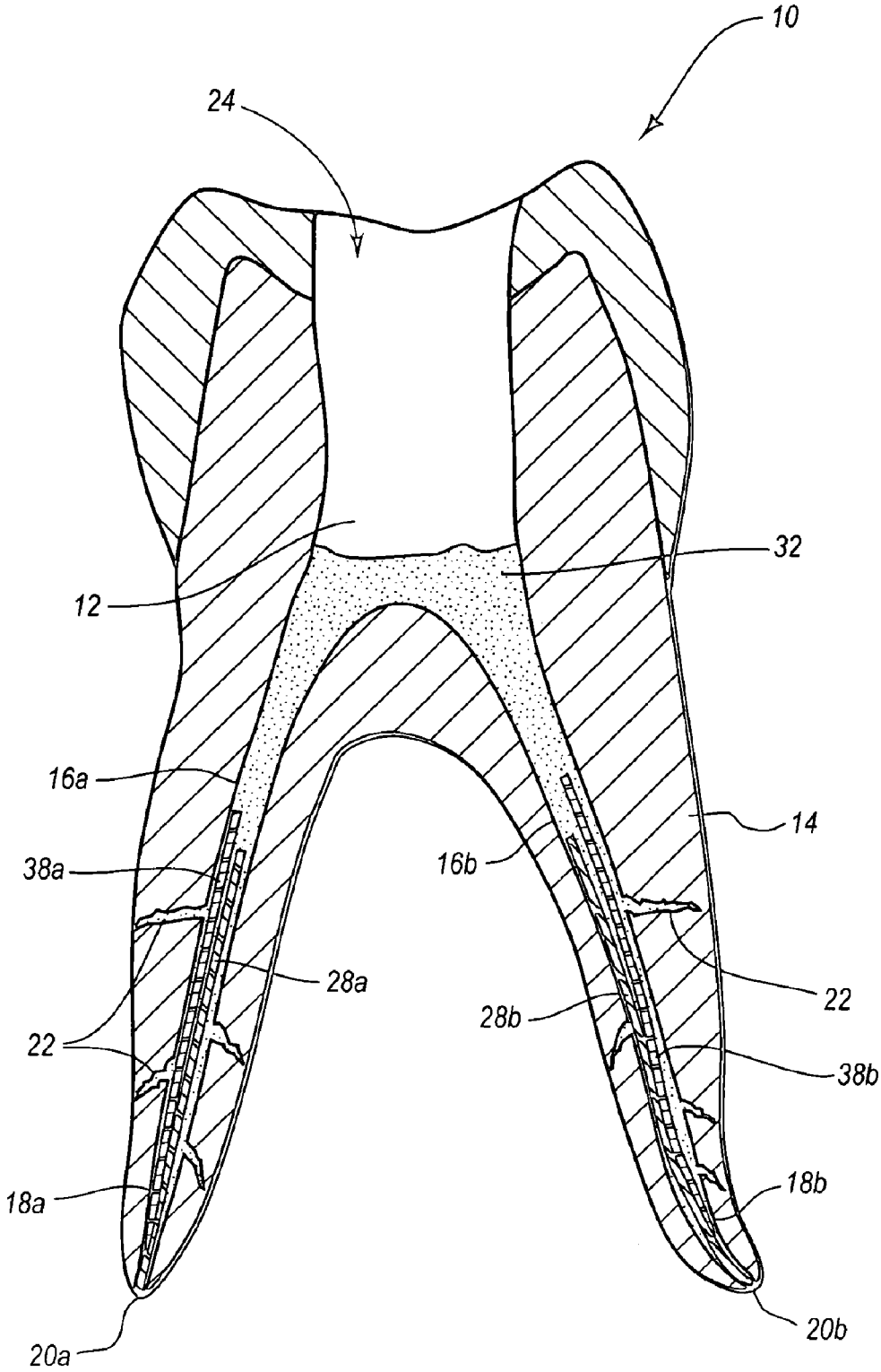
FIG. 6 shows the tooth and filler or sealer composition of FIG. 4 with a pair of activating accessory endodontic points placed in the sealer or filler composition to initiate or accelerate curing.

Once the practitioner has completed or performed, the desired dental procedures, an activating implement is inserted into the root canal in order to initiate or accelerate curing of the sealing resin contained in the root canal. By way of example, activating accessory endodontic points 38a and 38b can be placed in root canal 12 as shown in FIG. 6. The curing agent coated on or impregnated within accessory endodontic points 38a and 38b comes into contact with the sealer or filler composition and initiates curing. Because the practitioner has already had time to perform necessary procedures, sufficient curing agent can be included such that accessory points 38a and 38b cause sealer or filling material 32 to cure very rapidly. The accessory points can be made according to any of the methods described above. For example, the accessory points can be pre-coated or impregnated during manufacture, or they can be activated just prior to use.

In an alternative embodiment, a dental tool such as syringe 30 can be used to initiate or increase curing of the sealer or filler material. For, example, during an endodontic procedure, when the practitioner desires to have the sealer or filling agent cured, the practitioner can dip a syringe cannula 34 in a curing material and then place the coated syringe in contact with the sealer or filler composition.

In another alternative embodiment, the activating dental tool can be an endodontic file or other narrow gauge structure that is able to be inserted at least partially into a root canal.

In yet another alternative embodiment, the activating dental tool can be an implement or substrate that is simply a piece of plastic or other material that is made activating by applying a curing agent thereto. At least a portion of the plastic or other material is sized and configured to be placed in the root canal of a person or animal such that it can be inserted into the root canal and placed in contact with the sealer or filler composition.

In some cases, the circumstances of the procedure will determine which activating endodontic point or dental tool the practitioner will use. One advantage of a dental tool such as a piece of plastic is that it can be used at anytime without regard to its use in the dental procedure. In contrast, placement of an endodontic point is sometimes determined according to the needs of the procedure. However, using an activating endodontic point can be advantageous because the endodontic point is intended to permanently remain in the cured product.

V. KITS FOR USE IN CONTROLLING CURE TIMES

In order to further assist a practitioner in controlling cure times of an endodontic filler or sealer composition, one or more of several possible kits can be provided. It is within the scope of the invention to provide curing compositions having differing concentrations and/or amounts of curing agent in order to provide different cure times. Thus, according to one exemplary embodiment, a kit for use in initiating or accelerating curing of an endodontic filler or sealer composition may include one or more microdose containers, each containing an appropriate quantity and/or concentration of curing composition. In this embodiment, a dental practitioner can select an appropriate composition from the kit and dip an implement or substrate into the curing agent composition so as to form the activating implement or substrate just prior to use. The dental practitioner can control the cure time by selecting the proper curing agent composition.

In an alternative embodiment, one or more containers (e.g., microdose containers) containing one or more different quantities and/or concentrations of curing composition are provided together with one or more implements (e.g., gutta percha cones and/or rigid elongated devices, such as narrow plastic or metal rods, able to fit into a root canal). The one or more implements may be coated and/or impregnated with the curing composition by the practitioner just prior to inserting an implement within a filler or sealer composition placed within a root canal to initiate and/or accelerate curing thereof.

In another embodiment, kits within the scope of the invention may include one or more endodontic filler or sealer compositions and one or more microdose containers that contain appropriate amounts and/or concentrations of curing composition (e.g., to provide single or variable cure times). The endodontic filler or sealer composition may be pre-packaged within an appropriate container, such as a syringe. One or more syringe tips containing a cannula sufficiently narrow to be placed within a root canal may optionally be provided with the kit. The curing composition may include, as the "curing agent", one part of a multi-part curing system. The filler or sealer compositions may include another part of the multi-part curing system complementary to the curing agent within the curing composition. They may also comprise two-part chemical cure compositions that include a deficient amount of curing agent when mixed so that only slow or incomplete curing occurs. The curing composition is then used to merely accelerate rather than initiate curing. Such kits may optionally include one or more implements as previously discussed.

In an alternative embodiment, kits may be provided that include a plurality of implements that are pre-coated or impregnated with a curing agent. In one embodiment, the implements may include different amounts of curing agent so as to provide different cure times. The kit may include endodontic cones that are intended to be sequentially placed into a root canal during a filling or sealing procedure. In such case, one or more cones that are to be placed first may include an amount of curing agent that only initiates slow curing of the filler or sealer composition. One or more cones that are to be placed later may include an amount of curing agent that more rapidly cures the filler or sealer composition.

For example, a kit containing one or more master cones and one or more accessory cones can be used to select when or how fast to initiate the curing process. According to one embodiment, the master cone may be treated with a curing agent to initiate either slow or fast curing. Accessory cones designed to be placed into a root canal after the master cone can be treated with a curing agent. In the case where the master cone is treated to initiate slower curing one or more accessory cones can be used to initiate faster curing. In some cases only the accessory cones will be treated such that the master cone does not itself initiate curing.

According to one embodiment, the plurality of activating endodontic points and/or dental tools can have different concentrations of the curing agents and are included in a kit. The endodontic points or dental tools have different concentrations of curing agent that correspond to different cure times. During an endodontic procedure, the dental practitioner can select an activating endodontic point or dental tool that provides the proper cure time for that particular procedure.

During an endodontic procedure, those skilled in the art will know how much time they will need before the sealer or filler composition hardens. The present invention provides the practitioner with the ability to select any desired curing time during the procedure. If the practitioner needs 1 minute, 10 minutes, 2 hours or any other amount of time, the practitioner can select an activating endodontic point or dental tool with a curing agent in a concentration that provides the desired cure time. According to one embodiment, the endodontic filling or sealing composition will be a chemical cure composition having an initial cure time of about 15 minutes or more (e.g. EndoREZ®, which is sold by Ultradent Products, Inc.). The activating implements are preferably formulated so as to reduce the cure time to about 5 minutes or less.

In addition to providing controlled timing, the activating endodontic points and dental tools of the present invention can provide convenience. For example, a practitioner may want to use an activating master endodontic point even though curing would begin as soon as the sealer or filler composition is placed in the root canal. In this embodiment, the practitioner can eliminate the need to mix the sealer or filler composition, thus making the endodontic procedure more convenient. Furthermore, the practitioner can be provided with a set of activating endodontic points that give the practitioner a selection of different concentrations of curing agent and thus different cure times.

The present invention is also not limited with respect to use of a single activating endodontic point or dental tool during an endodontic procedure. For example, an activating master endodontic point can be used with an activating accessory endodontic point. The master endodontic point can initiate relatively slow curing and the accessory endodontic point can be used to accelerate curing. In yet another embodiment, a master endodontic point, an accessory endodontic point, and/or a dental tool can be used to cure the sealer or filling material. Each activating point or tool can be coated and/or impregnated with the same or differing concentrations of curing agent and can be placed in contact with the same or different portions of the sealer or filling material.

The present invention also includes using more than one type of curing system. For example, a chemical curing system can be used in conjunction with a heat curing system or a light curing system. Those skilled in the art will recognize the many different combinations of curing systems that can be used with the foregoing teachings of the present invention.

The following examples provide specific formulas of exemplary embodiments of the present invention and should be considered as illustrative of the present invention and not limiting in any way.

VI. EXAMPLES

The following are examples provided in order to further assist one of skill in the art in practicing the invention. They are given only by way of example and should not be construed as being the only way to practice the invention. One of skill in the art can modify or enhance any of the following examples as needed to yield a composition or activating implement having any desired property.

Example 1

Acrylate Resin Coating

In Examples 2-5, below, a curing agent is diluted in an acrylate resin coating. The coating provides for better adhesion between the curing agent and a gutta percha cone. Diluting the curing agent in the acrylate resin also gives the coating a desired cure time. The acrylate resin coating used in the formulas of examples 2-5 is prepared by first preparing a prepolymer mixture according to the following formula:

| | |
|---|---|
| Krasol LBH 2000 (linear polybutadiene polymer with hydroxyl end groups) | 80.499% |
| Dabc LBH 2000 (tin catalyst) | 0.001% |
| Desmodur W bis(4-isocynotocyclohexyl) methane | 19.500% |

The prepolymer formed using the foregoing components is used to form an acrylate resin coating according to the following formula:

| | |
|---|---|
| Prepolymer | 2.5% |
| 2-hydroxyethyl acrylate | 2.5% |
| Polyethylene glycol diacrylate | 70.8% |

The prepolymer and the 2-hydroxyethyl acrylate are allowed to react to completion and are then directly mixed with the polyethylene glycol diacrylate to form the Acrylate Resin Coating. In each of Examples 2-5, an endodontic point was coated or impregnated with the curing composition and then placed in an acrylate-based sealer or filler composition in order to initiate curing. The acrylate-based sealer or filler composition included benzoyl peroxide as an initiator. The amount of sealer or filler composition used in the study was similar to the amount that would occupy a typical root canal.

Example 2

A curing composition used to coat an endodontic cone was made by mixing together the following components:

| | |
|---|---|
| Acrylate Resin Coating | 37.5% |
| Triethylene glycol dimethacrylate | 37.0% |
| P-TIDE (amine curing agent) | 25.0% |
| IRGACURE (a photoinitiator) | 0.5% |

An endodontic cone made from gutta percha was coated or impregnated with the foregoing curing composition. The curing composition was solidified using light initiated curing. The coated endodontic cone was placed into a quantity of filler or sealer composition constituting a typical amount found within a root canal. The amine curing agent caused the sealer or filler composition to cure in about 2 minutes at 37° C.

Example 3

A curing composition used to coat an endodontic cone was made by mixing together the following components:

| | |
|---|---|
| Acrylate Coating | 97.5% |
| DMPT | 2.0% |
| Irgacure | 0.5% |

An endodontic cone made from gutta percha was coated or impregnated with the foregoing curing composition. The curing composition was solidified using light initiated curing. The coated endodontic cone was placed into a quantity of filler or sealer composition constituting a typical amount found within a root canal. The amine curing agent caused the sealer or filler composition to cure in about 8 minutes at 37° C.

Example 4

A curing composition used to coat an endodontic cone was made by mixing together the following components:

| | |
|---|---|
| Acrylate Resin Coating | 98.0% |
| P-TIDE | 1.5% |
| Irgacure | 0.5% |

An endodontic cone made from gutta percha was coated or impregnated with the foregoing curing composition. The curing composition was solidified using light initiated curing. The coated endodontic cone was placed into a quantity of filler or sealer composition constituting a typical amount found within a root canal. The amine curing agent caused the sealer or filler composition to cure in about 18 minutes at 37° C. The activating endodontic cone made according to this example gave inconsistent results.

Example 5

A curing composition used to coat an endodontic cone was made by mixing together the following components:

| | |
|---|---|
| Toluene | 90.0% |
| P-TIDE | 10.00% |

An endodontic cone made from gutta percha was impregnated with the foregoing composition by briefly immersing the endodontic cone in the solution and then allowing the solvent to volatize. The endodontic cone was then placed in the sealer or filler composition, which caused curing in about 3 minutes at 37° C. The P-TIDE degraded over time, thus reducing the effectiveness of the activating endodontic cone over a period of several months.

Example 6

An endodontic cone was impregnated with the following curing composition by immersing the endodontic cone in the composition. The endodontic cone was placed in a sealer or filler composition, which accelerated to initial curing time from 15 minutes to 5 minutes at 37° C.

| | |
|---|---|
| TEG-DMA | 74.9% |
| P-TIDE | 25% |
| BHT | 0.1% |

Example 7

An endodontic cone is impregnated with the following curing composition by immersing the endodontic cone in the composition. The endodontic cone is placed in a sealer or filler composition in order to accelerate curing.

| | |
|---|---|
| TEG-DMA | 74.9% |
| DMPT | 25% |
| BHT | 0.1% |

Example 8

An endodontic cone was impregnated with the following curing composition by immersing the endodontic cone in the composition.

| | |
|---|---|
| TEG-DMA | 49.97% |
| P-TIDE | 50.00% |
| Methyl Hydroquinone (stabilizer) | 0.03% |

The endodontic cone was placed into EndoREZ and was able to accelerate the curing time from 15-30 minutes down to 3-5 minutes.

Example 9

An endodontic cone was impregnated with the following curing composition by immersing the endodontic cone in the composition.

| | |
|---|---|
| TEG-DMA | 24.97% |
| P-TIDE | 75.00% |
| Methyl Hydroquinone (stabilizer) | 0.03% |

The endodontic cone was placed into EndoREZ and was able to accelerate the curing time from 15-30 minutes down to 3-5 minutes.

Example 10

An endodontic cone was impregnated with the following curing composition by immersing the endodontic cone in the composition.

| | |
|---|---|
| TEG-DMA | 24.97% |
| DMPT | 75.00% |
| Methyl Hydroquinone (stabilizer) | 0.03% |

The endodontic cone was placed into EndoREZ and was able to accelerate the curing time from 15-30 minutes down to about 3 minutes.

Example 11

An endodontic cone was impregnated with the following curing composition by immersing the endodontic cone in the composition.

| | |
|---|---|
| TEG-DMA | 49.97% |
| DMPT | 50.00% |
| Methyl Hydroquinone (stabilizer) | 0.03% |

The endodontic cone was placed into EndoREZ and was able to accelerate the curing time from 15-30 minutes down to about, 3 minutes.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A curing composition for use in initiating or accelerating curing of a filler or sealer composition placed in a root canal of a tooth, the curing composition consisting essentially of:

a liquid carrier in an amount of 0% to about 75%; and a curing agent that is only one part of a multi-part chemical curing system in order to initiate or accelerate curing of a filler or sealer composition placed within a root canal of a tooth which contains a complementary part of the multi-part chemical curing system, wherein the curing agent has a concentration in a range of about 25% to 100% by weight of the curing composition, wherein the curing agent does not react until contacted with a filler or sealer composition containing a complementary part of the multi-part chemical curing system, the curing composition having a flowability so as to facilitate coating onto or impregnation within an implement that is sized so as to be at least partially insertable into a root canal of a tooth.

2. A curing composition as defined in claim 1, wherein the liquid carrier comprises a non-polymerizable solvent.

3. A curing composition as defined in claim 1, wherein the liquid carrier comprises a polymerizable hydrophilic resin.

4. A curing composition as defined in claim 1, wherein the curing agent is an additive compound that destabilizes a peroxide initiator contained in a sealer or filler composition.

5. A curing composition as defined in claim 4, wherein the additive compound comprises an amine selected from the group consisting of dimethylamino ethyl methacrylate, triethyl amine, 2-dimethylamino ethanol, diethylamino ethyl methacrylate, trihexyl amine, N,N-dimethyl-p-toluidine, N-methylethanolamine, 2,2'(p-tolyimino) diethanol, derivatives thereof, and combinations thereof.

6. A curing composition as defined in claim 1, wherein the curing agent is an initiator that is destabilized by an additive compound contained in a sealer or filler composition.

7. A curing composition as defined in claim 6, wherein the initiator comprises a peroxide selected from the group consisting of benzoyl peroxide, 2-butanone peroxide, lauroyl peroxide, tert-butyl peroxide, derivatives thereof, and combinations thereof.

8. A curing composition as defined in claim 1, wherein the curing agent is selected to catalyze an epoxy-based polymer composition.

9. A curing composition as defined in claim 8, wherein the curing agent is selected from the group consisting of strong bases, amines, and hexamethylenetramine.

10. A curing composition as defined in claim 1, wherein the curing agent is selected to catalyze a cationic-based polymer composition.

11. A curing composition as defined in claim 1, wherein the curing agent has a concentration in a range of about 35% to about 75% by weight of the curing composition.

12. A curing composition as defined in claim 1, wherein the curing agent has a concentration in a range of about 45% to about 55% by weight of the curing composition.

13. A curing composition as defined in claim 1, wherein the curing composition is pre-packaged in a microdose container.

14. A curing composition as defined in claim 13, wherein the microdose container contains from about 0.01 ml to about 1 ml of the curing composition.

15. A curing composition as defined in claim 13, wherein the microdose container contains from about 0.05 ml to about 0.5 ml of the curing composition.

16. A curing composition as defined in claim 13, wherein the microdose container contains from about 0.075 ml to about 2.5 ml of the curing composition.

17. A kit for use in controlling cure time of a filler or sealer composition comprising the curing composition of claim 1 pre-packaged within a plurality of microdose containers.

18. A kit as defined in claim 17, wherein the kit comprises at least two microdose containers containing different concentrations and/or amounts of the curing agent.

19. A kit for use in controlling cure time of a filler or sealer composition comprising the curing composition of claim 1 and a filler or sealer composition containing a complementary part of the multi-part chemical curing system.

20. A kit for use in controlling cure time of a filler or sealer composition comprising the curing composition of claim 1 and one or more implements for introducing the curing composition into a root canal of a tooth and that are sized so as to be at least partially insertable into a root canal of a tooth.

21. A kit as defined in claim 20, wherein the one or more implements comprise one or more gutta percha cones.

22. A kit for use in initiating or accelerating curing of a filler or sealer composition placed in a root canal of a tooth, comprising:

an endodontic filler or sealer composition stored in a first container and containing a first part of a multi-part chemical curing system; and a curing composition stored in a second container and which contains a curing agent that is only a complementary part of the multi-part chemical curing system in order to initiate or accelerate curing of the filler or sealer composition when contacted therewith in a root canal of a tooth, wherein the curing agent has a concentration in a range of about 25% to 100% by weight of the curing composition, wherein the curing agent does not react until contacted with the endodontic filler or sealer composition containing the first part of the multi-part chemical curing system, the curing composition having a flowability so as to facilitate coating onto or impregnation within an implement that is sized so as to be at least partially insertable into a root canal of a tooth.

23. A kit as defined in claim 22, wherein the filler or sealer composition contains a peroxide initiator and the curing composition contains an amine additive that destabilizes the peroxide initiator when the curing composition is contacted with the filler or sealer composition.

24. A kit as defined in claim 22, wherein the curing composition contains a peroxide initiator and the filler or sealer composition contains an amine additive that destabilizes the peroxide initiator when the curing composition is contacted with the filler or sealer composition.

25. A kit for use in initiating or accelerating curing of a filler or sealer composition placed in a root canal of a tooth, comprising:

a curing composition containing a curing agent that is only one part of a multi-part chemical curing system in order to initiate or accelerate curing of a filler or sealer composition placed within a root canal of a tooth which contains a complementary part of the multi-part chemical curing system, wherein the curing agent has a concentration of at least about 25% by weight of the curing composition, wherein the curing agent does not react until contacted with a filler or sealer composition containing a complementary part of the multi-part chemical curing system, the curing composition having a flowability so as to facilitate coating onto or impregnation within an implement that is sized so as to be at least partially insertable into a root canal of a tooth; and a plurality of implements that are sized so as to be at least partially insertable within a root canal of a tooth in order to facilitate contact of the curing composition with a filler or sealer composition placed within a root canal of a tooth, wherein coating or impregnating one of the implements with the curing agent yields a coated or impregnated implement that is sized so as to be at least partially insertable into a root canal of a tooth.

26. A kit as defined in claim 25, wherein the implements comprise one or more endodontic cones.

27. A kit as defined in claim 25, wherein the implements comprise one or more dental tools.

28. A kit as defined in claim 25, wherein the implements comprise one or more plastic fragments.

*29. A curing composition for use in initiating curing of a filler or sealer composition placed in a root canal of a tooth, the curing composition consisting essentially of:*

*a liquid carrier and*

*a curing agent that is only one part of a multi-part chemical curing system in order to initiate curing of a filler or sealer composition placed within a root canal of a tooth which contains a complementary part of the multi-part chemical curing system,*

*wherein the curing agent has a concentration in a range of about 5% to 35% by weight of the curing composition,*

*wherein the curing agent does not react until contacted with a filler or sealer composition containing a complementary part of the multi-part chemical curing system,*

*the curing composition having a flowability so as to facilitate coating onto or impregnation within an implement that is sized so as to be at least partially insertable into a root canal of a tooth.*

*30. A curing composition as defined in claim 29, wherein the curing agent has a concentration in a range of about 5% to 25% by weight of the curing composition.*

*31. A curing composition as defined in claim 29, wherein the curing agent has a concentration in a range of about 20% to 25% by weight of the curing composition.*

*32. A curing composition as defined in claim 29, wherein the liquid carrier comprises a non-polymerizable solvent.*

*33. A curing composition as defined in claim 29, wherein the liquid carrier comprises a polymerizable hydrophilic resin.*

*34. A curing composition as defined in claim 29, wherein the curing agent is an additive compound that destabilizes a peroxide initiator contained in a sealer or filler composition.*

*35. A curing composition as defined in claim 34, wherein the additive compound comprises an amine selected from the group consisting of dimethylamino ethyl methacrylate, triethyl amine, 2-dimethylamino ethanol, diethylamino ethyl methacrylate, trihexyl amine, N,N-dimethyl-p-toluidine, N-methylethanolamine, 2,2'(p-tolyimino) diethanol, derivatives thereof, and combinations thereof.*

*36. A curing composition as defined in claim 29, wherein the curing agent is an initiator that is destabilized by an additive compound contained in a sealer or filler composition.*

*37. A curing composition as defined in claim 36, wherein the initiator comprises a peroxide selected from the group consisting of benzoyl peroxide, 2-butanone peroxide, lauroyl peroxide, tert-butyl peroxide, derivatives thereof, and combinations thereof.*

*38. A curing composition as defined in claim 29, wherein the curing agent is selected to catalyze an epoxy-based polymer composition.*

*39. A curing composition as defined in claim 38, wherein the curing agent is selected from the group consisting of strong bases, amines, and hexamethylenetramine.*

*40. A curing composition as defined in claim 29, wherein the curing agent is selected to catalyze a cationic-based polymer composition.*

*41. A curing composition as defined in claim 29, wherein the curing composition is pre-packaged in a microdose container.*

*42. A curing composition as defined in claim 41, wherein the microdose container contains from about 0.01 ml to about 1 ml of the curing composition.*

*43. A curing composition as defined in claim 41, wherein the microdose container contains from about 0.05 ml to about 0.5 ml of the curing composition.*

*44. A curing composition as defined in claim 41, wherein the microdose container contains from about 0.075 ml to about 2.5 ml of the curing composition.*

*45. A kit for use in initiating curing of a filler or sealer composition comprising the curing composition of claim 29 pre-packaged within a plurality of microdose containers.*

*46. A kit as defined in claim 45, wherein the kit comprises at least two microdose containers containing different concentrations and/or amounts of the curing agent.*

*47. A kit for use in initiating curing of a filler or sealer composition comprising the curing composition of claim 29 and a filler or sealer composition containing a complementary part of the multi-part chemical curing system.*

*48. A kit for use in initiating curing of a filler or sealer composition comprising the curing composition of claim 29 and one or more implements for introducing the curing composition into a root canal of a tooth and that are sized so as to be at least partially insertable into a root canal of a tooth.*

*49. A kit as defined in claim 48, wherein the one or more implements comprise one or more gutta percha cones.*

*50. A kit for use in initiating curing of a filler or sealer composition placed in a root canal of a tooth comprising:*

*an endodontic filler or sealer composition stored in a first container and containing a first part of a multi-part chemical curing system; and*

*a curing composition stored in a second container and which contains a curing agent that is only a complementary part of the multi-part chemical curing system in order to initiate curing of the filler or sealer composition when contacted therewith within a root canal of a tooth,*

*wherein the curing agent has a concentration in a range of about 5% to 35% by weight of the curing composition,*

*wherein the curing agent does not react until contacted with the endodontic filler or sealer composition containing the first part of the multi-part chemical curing system,*

*the curing composition having a flowability so as to facilitate coating onto or impregnation within an implement that is sized so as to be at least partially insertable into a root canal of a tooth.*

*51. A kit as defined in claim 50, wherein the curing agent has a concentration in a range of about 5% to 25% by weight of the curing composition.*

*52. A kit as defined in claim 50, wherein the filler or sealer composition contains a peroxide initiator and the curing composition contains an amine additive that destabilizes the peroxide initiator when the curing composition is contacted with the filler or sealer composition.*

*53. A kit as defined in claim 50, wherein the curing composition contains a peroxide initiator and the filler or sealer composition contains an amine additive that destabilizes the peroxide initiator when the curing composition is contacted with the filler or sealer composition.*

*54. A kit for use in initiating curing of a filler or sealer composition placed in a root canal of a tooth comprising:*

*a curing composition containing a curing agent that is only one part of a multi-part chemical curing system in order to initiate or accelerate curing of a filler or sealer composition placed within a root canal of a tooth which contains a complementary part of the multi-part chemical curing system,*

*wherein the curing agent has a concentration of about 5% to about 35% by weight of the curing composition,*

*wherein the curing agent does not react until contacted with a filler or sealer composition containing a complementary part of the multi-part chemical curing system*

*the curing composition having a flowability so as to facilitate coating onto or impregnation within an implement that is sized so as to be at least partially insertable into a root canal of a tooth; and*

*a plurality of implements that are sized so as to be at least partially insertable within a root canal of a tooth in order to facilitate contact of the curing composition with a filler or sealer composition placed within a root canal of a tooth,*

*wherein coating or impregnating one of the implements with the curing agent yields a coated or impregnated implement that is sized so as to be at least partially insertable into a root canal of a tooth.*

*55. A kit as defined in claim 54, wherein the curing agent has a concentration in a range of about 5% to 25% by weight of the curing composition.*

*56. A kit as defined in claim 54, wherein the implements comprise one or more endodontic cones.*

*57. A kit as defined in claim 54, wherein the implements comprise one or more dental tools.*

*58. A kit as defined in claim 54, wherein the implements comprise one or more plastic fragments.*

*59. A curing composition for use in initiating curing of a filler or sealer composition placed in a root canal of a tooth, the curing composition consisting essentially of:*

*a non-polymerizable liquid carrier; and*

*a curing agent that is only one part of a multi-part chemical curing system in order to initiate curing of a filler or sealer composition placed within a root canal of a tooth which contains a complementary part of the multi-part chemical curing system,*

*wherein the curing agent has a concentration in a range of about 0.1% to 35% by weight of the curing composition,*

*wherein the curing agent does not react until contacted with a filler or sealer composition containing a complementary part of the multi-part chemical curing system,*

*the curing composition having a flowability so as to facilitate coating onto or impregnation within an implement that is sized so as to be at least partially insertable into a root canal of a tooth.*

*60. A curing composition as defined in claim 59, wherein the non-polymerizable liquid carrier is a non-polymerizable solvent selected from the group consisting of water, methanol, ethanol, isopropyl alcohol, propylene glycol, 1,3-propanediol, glycerin, polyethylene glycol, polypropylene glycol, actone, toluene, xylene, ethyl acetate, DMSO, DMF, acetonitrile, and mixtures thereof.*

*61. A curing composition as defined in claim 59, wherein the curing agent has a concentration in a range of about 0.1% to 20% by weight of the curing composition.*

*62. A curing composition as defined in claim 59, wherein the curing agent has a concentration in a range of about 1% to 2% by weight of the curing composition.*

*63. A curing composition as defined in claim 59, wherein the curing agent is an additive compound that destabilizes a peroxide initiator contained in a sealer or filler composition.*

*64. A curing composition as defined in claim 63, wherein the additive compound comprises an amine selected from the group consisting of dimethylamino ethyl methacrylate, triethyl amine, 2-dimethylamino ethanol, diethylamino ethyl methacrylate, trihexyl amine, N,N-dimethyl-p-toluidine, N-methylethanolamine, 2,2'(p-tolyimino) diethanol, derivatives thereof, and combinations thereof.*

* * * * *